United States Patent
Jiang et al.

(10) Patent No.: US 9,528,042 B1
(45) Date of Patent: *Dec. 27, 2016

(54) DRILLING FLUID ADDITIVE COMPOSITION AND SUPER HIGH TEMPERATURE SUPER HIGH DENSITY CLAY-FREE OIL-IN-WATER DRILLING FLUID

(71) Applicant: China University of Petroleum (Beijing), Beijing (CN)

(72) Inventors: Guancheng Jiang, Beijing (CN); Zhengqiang Deng, Beijing (CN); Yinbo He, Beijing (CN); Xianbin Huang, Beijing (CN); Fan Liu, Beijing (CN); Yang Xuan, Beijing (CN); Zepu Cheng, Beijing (CN); Lili Yang, Beijing (CN); Chunlei Wang, Beijing (CN); Shuanglei Peng, Beijing (CN); Chong Liu, Beijing (CN); Kai Wang, Beijing (CN); Xinliang Li, Beijing (CN); Yawei Shi, Beijing (CN)

(73) Assignee: China University of Petroleum (Beijing), Beijing (CN)

( * ) Notice: Subject to any disclaimer, the term of this patent is extended or adjusted under 35 U.S.C. 154(b) by 0 days.

This patent is subject to a terminal disclaimer.

(21) Appl. No.: 15/136,496

(22) Filed: Apr. 22, 2016

(30) Foreign Application Priority Data

Jan. 28, 2016 (CN) .......................... 2016 1 0059057

(51) Int. Cl.
| | | |
|---|---|---|
| *C09K 8/36* | (2006.01) | |
| *C09K 8/28* | (2006.01) | |
| *C09K 8/035* | (2006.01) | |
| *C07C 231/02* | (2006.01) | |

(52) U.S. Cl.
CPC ............... *C09K 8/28* (2013.01); *C07C 231/02* (2013.01); *C09K 8/035* (2013.01)

(58) Field of Classification Search
None
See application file for complete search history.

(56) References Cited

U.S. PATENT DOCUMENTS

| | | | |
|---|---|---|---|
| 4,501,672 A | 2/1985 | Connell et al. | |
| 9,365,762 B1 * | 6/2016 | Jiang | C09K 8/36 |
| 2006/0116296 A1 * | 6/2006 | Kippie | C09K 8/12 |
| | | | 507/244 |

FOREIGN PATENT DOCUMENTS

| | | |
|---|---|---|
| CN | 103980869 A | 8/2014 |
| CN | 104861944 A | 8/2015 |
| CN | 104893691 A | 2/2016 |

* cited by examiner

*Primary Examiner* — John J Figueroa
(74) *Attorney, Agent, or Firm* — Calfee, Halter & Griswold LLP

(57) ABSTRACT

The present invention relates to the field of petrochemical drilling and discloses a drilling fluid additive composition. The composition contains an emulsifier and a rheological modifier. The emulsifier is one or more of the compounds represented by Formula (1); the rheological modifier is dimer acid-organic amine copolymer, comprising structural units from the dimer acid, structural units from the alkylamine and structural units from the arylamine. The present invention further provides a drilling fluid containing the foregoing composition. When a clay-free oil-in-water drilling fluid contains the drilling fluid additive composition of the present invention containing the emulsifier and rheological modifier, it may have high temperature resistance and high density;

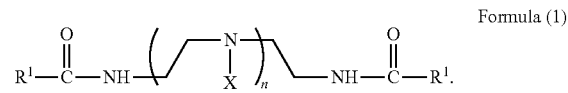

Formula (1)

20 Claims, No Drawings

DRILLING FLUID ADDITIVE COMPOSITION AND SUPER HIGH TEMPERATURE SUPER HIGH DENSITY CLAY-FREE OIL-IN-WATER DRILLING FLUID

CROSS REFERENCE TO RELATED APPLICATIONS

This application claims priority to Chinese Application No. 201610059057.8, filed on Jan. 28, 2016, entitled "Drilling Fluid Additive Composition and Super High Temperature Super High Density Clay-Free Oil-in-Water Drilling Fluid", which is specifically and entirely incorporated by reference.

FIELD

The present invention relates to the field of petrochemical drilling, particularly to a drilling fluid additive composition, and a super high temperature super high density clay-free oil-in-water drilling fluid.

BACKGROUND

Oil-based drilling fluid is a drilling fluid with oil as a continuous phase. Compared with water-based drilling fluid, oil-based drilling fluid has such advantages as strong inhibitive ability, good lubricity, resistance to salt contamination, resistance to calcium contamination and small damage to oil and gas reservoir. Obviously, the strong inhibitive ability, strong lubricity and good reservoir protection capability of oil-based drilling fluid make it more suitable to well drilling of building up sections and long horizontal sections. However, the prior art of oil-based drilling fluid is still not perfect, as mainly manifested in the following few aspects.

(1) Inadequate high temperature resistance property: with the increase of well depth and the rise of bottom well temperature, the requirement for temperature resistance of oil-based drilling fluid increases, too.

(2) Universally low density: oil-based drilling fluid with ordinary density no longer can meet the requirements of high pressure formation for the density of drilling fluid, while raising density of drilling fluid will bring about problems like poor rheological behavior.

The clay-phase oil-in-water drilling fluid improves the suspension property of the oil-based drilling fluid system mainly through organic clay. Typical composition is: base oil or synthetic base oil serving as an external phase; organic salt, dissolved in internal phase water (typically, is a 30% $CaCl_2$ aqueous solution); other additives, such as suspending agent, filtrate reducer, humectant, emulsifier and rheological modifier. As organic clay is used as a clay phase, the clay-phase oil-in-water drilling fluid has the problems of poor temperature resistance, large damage to reservoir and low density. In comparison, the current clay-free oil-in-water drilling fluid uses rheological modifier to replace the clay phase in the clay-phase oil-in-water drilling fluid. As a result, the drilling fluid has the advantages of resistance to high temperature, low damage to reservoir and high density, but the current clay-free oil-in-water drilling fluid still can hardly obtain super high temperature resistance and super high density and realize exploitation of oil and gas from high pressure deep wells.

SUMMARY

An object of the present invention is to overcome the defects of current clay-free oil-in-water drilling fluid, including poor temperature resistance and low density, and provide a drilling fluid additive composition that still can obtain a drilling fluid with high temperature resistance and high density even without a clay phase, and a super high temperature super high density clay-free oil-in-water drilling fluid.

In order to realize the above object, the present invention provides a drilling fluid additive composition, wherein the composition comprises an emulsifier and a rheological modifier; the emulsifier is one or more of the compounds represented by following Formula (1); the rheological modifier is dimer acid-organic amine copolymer comprising structural units from dimer acid, structural units from alkylamine and structural units from arylamine, of which the dimer acid is a dimer of oleic acid and linoleic acid, the alkylamine is one or more of C10-C20 alkyl primary amines, and the arylamine is one or more of aniline and aniline substituted by C1-C3 alkyl at one or more sites on benzene ring, Formula (1)

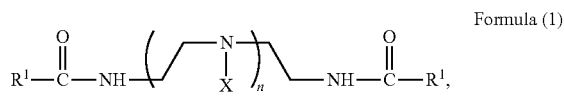

in Formula (1), each of the two $R^1$ groups is independently selected from C14-C30 alkyl optionally substituted by group Y and C14-C30 unsaturated alkyl with a carbon-carbon double bond optionally substituted by group Y, and the group Y is independently selected from the groups shown in the following formula:

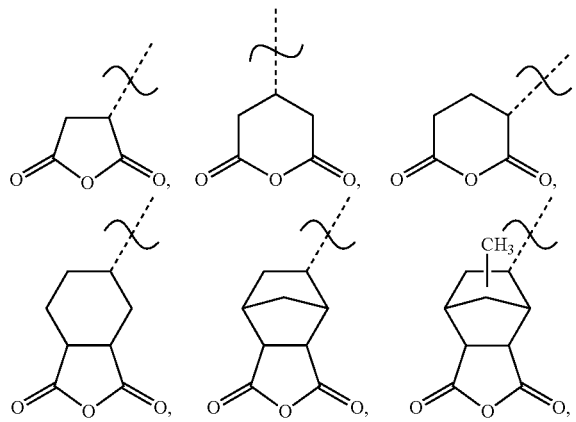

n is an integer of 1-8;
n X-es are independently selected from H and —C(O)—$R^2$, and at least one X is —C(O)—$R^2$, $R^2$ is selected from carboxyl, C1-C6 alkyl, C3-C8 cycloalkyl, C1-C6 alkyl substituted by carboxyl, C3-C8 cycloalkyl substituted by carboxyl, C3-C8 cycloalkyl substituted by carboxyl and C1-C4 alkyl, C2-C6 unsaturated alkyl with a carbon-carbon double bond, C3-C8 unsaturated cycloalkyl with a carbon-carbon double bond, C2-C6 unsaturated alkyl with a carbon-carbon double bond substituted by carboxyl, and C3-C8 unsaturated cycloalkyl with a carbon-carbon double bond substituted by carboxyl and C1-C4 alkyl.

The present invention further provides a super high temperature super high density clay-free oil-in-water drilling fluid containing the foregoing additive composition.

When a clay-free oil-in-water drilling fluid contains the drilling fluid additive composition of the present invention comprising the emulsifier and rheological modifier, it may have high temperature resistance property and high density. For example, the drilling fluid can resist a temperature of 240° C. or above and its density is 2.6 g/cm$^3$ or above.

Other features and advantages of the present invention will be elaborated in the subsequent embodiments.

DETAILED DESCRIPTION OF THE EMBODIMENTS

The embodiments of the present invention will be described in details below. It should be understood that the embodiments described here are only intended to illustrate and not to limit the present invention.

The present invention provides a drilling fluid additive composition, wherein the composition comprises an emulsifier and a rheological modifier; the emulsifier is one or more of the compounds represented by following Formula (1); the rheological modifier is dimer acid-organic amine copolymer comprising structural units from dimer acid, structural units from alkylamine and structural units from arylamine, of which the dimer acid is a dimer of oleic acid and linoleic acid, the alkylamine is one or more of C10-C20 alkyl primary amines, and the arylamine is one or more of aniline and aniline substituted by C1-C3 alkyl at one or more sites on benzene ring,

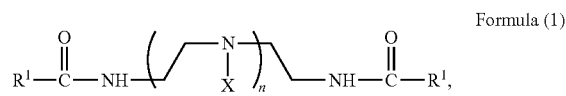

Formula (1)

in Formula (1), each of the two $R^1$ groups is independently selected from C14-C30 alkyl optionally substituted by group Y and C14-C30 unsaturated alkyl with a carbon-carbon double bond optionally substituted by group Y, and the group Y is independently selected from the groups shown in the following formula:

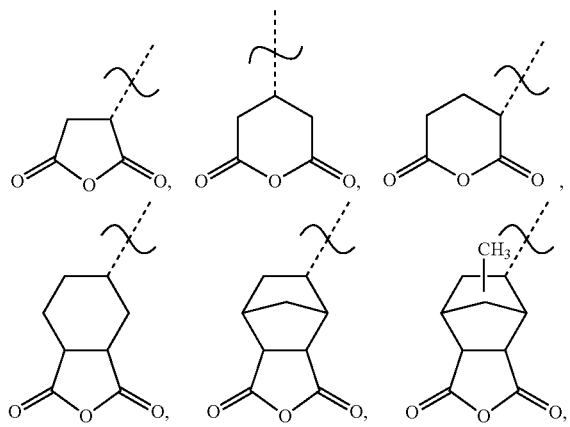

n is an integer of 1-8;

n X-es are independently selected from H and —C(O)—$R^2$, and at least one X is —C(O)—$R^2$, $R^2$ is selected from carboxyl, C1-C6 alkyl, C3-C8 cycloalkyl, C1-C6 alkyl substituted by carboxyl, C3-C8 cycloalkyl substituted by carboxyl, C3-C8 cycloalkyl substituted by carboxyl and C1-C4 alkyl, C2-C6 unsaturated alkyl with a carbon-carbon double bond, C3-C8 unsaturated cycloalkyl with a carbon-carbon double bond, C2-C6 unsaturated alkyl with a carbon-carbon double bond substituted by carboxyl, and C3-C8 unsaturated cycloalkyl with a carbon-carbon double bond substituted by carboxyl and C1-C4 alkyl.

According to the present invention, the emulsifier and rheological modifier may be used cooperatively at any ratio to obtain an additive composition that can promote drilling fluid to raise density and temperature resistance, but in order that the emulsifier and rheological modifier can cooperate with each other in a better way, the weight ratio of the emulsifier and rheological modifier is preferably 100:5 to 100:200, more preferably 100:5 to 100:100, still more preferably 100:10 to 100:80, most preferably 100:12 to 100:70, such as 100:25 to 100:50 (here the rheological modifier is measured based on the dimer acid-organic amine copolymer). Particularly preferably, the additive composition of the present invention is a combination of the emulsifier and the rheological modifier.

According to the present invention, the emulsifier is one or more of the compounds represented by the foregoing Formula (1). The compounds represented by Formula (1) are compounds with a comb-like structure containing a long saturated and/or unsaturated alkyl chains at two ends and short alkyl chains in the middle. Such compounds with a comb-like structure can realize the object of raising the density and temperature resistance of drilling fluid through increasing membrane strength of emulsification interface and stabilizing emulsion with the help of the rheological modifier.

Preferably, in Formula (1), each of the two $R^1$ groups is independently selected from C14-C20 alkyl optionally substituted by group Y and C14-C20 unsaturated alkyl with a carbon-carbon double bond optionally substituted by group Y (preferably with not more than 5 carbon-carbon double bonds, 1, 2 or 3 for example); n is an integer of 1-6; $R^2$ is selected from carboxyl, C1-C4 alkyl, C4-C6 cycloalkyl, C1-C4 alkyl substituted by carboxyl, C4-C6 cycloalkyl substituted by carboxyl, C4-C6 cycloalkyl substituted by carboxyl and methyl, C2-C4 unsaturated alkyl with a carbon-carbon double bond (preferably with 1-3 carbon-carbon double bonds, 1, 2 or 3 for example), C4-C6 unsaturated cycloalkyl with a carbon-carbon double bond (preferably with not more than 5 carbon-carbon double bonds, 1, 2 or 3 for example), C2-C4 unsaturated alkyl with a carbon-carbon double bond substituted by carboxyl (preferably with 1-3 carbon-carbon double bonds, 1, 2 or 3 for example), and C4-C7 unsaturated cycloalkyl with a carbon-carbon double bond substituted by carboxyl and methyl (preferably with not more than 5 carbon-carbon double bonds, 1, 2 or 3 for example).

More preferably, in Formula (1), each of the two $R^1$ groups is independently selected from C15-C18 alkyl optionally substituted by group Y and C15-C18 unsaturated alkyl with a carbon-carbon double bond optionally substituted by group Y; n is an integer of 1-4, for example 1, 2, 3 or 4.

According to the present invention, the two $R^1$ groups are selected independently and may be same or different. The embodiments of $R^1$ for example may include the following groups: —$(CH_2)_7$—CH=CH—$(CH_2)_7$—$CH_3$, —$(CH_2)_8$—CH(Y)—$(CH_2)_7$—$CH_3$, —$(CH_2)_7$—CH(Y)—$(CH_2)_8$—$CH_3$, —$(CH_2)_7$—CH(Y)—CH(Y)—$(CH_2)_7$—$CH_3$, —$(CH_2)_{16}$—$CH_3$, —$(CH_2)_7$—CH=CH—$CH_2$—CH=CH—$(CH_2)_4$—$CH_3$, —$(CH_2)_7$—CH=CH—$CH_2$—$CH_2$—CH(Y)—$(CH_2)_4$—$CH_3$, —$(CH_2)_7$—CH=CH—

CH$_2$—CH(Y)—(CH$_2$)$_5$—CH$_3$, —(CH$_2$)$_8$—CH(Y)—CH$_2$—CH=CH—(CH$_2$)$_4$—CH$_3$, —(CH$_2$)$_7$—CH(Y)—CH$_2$—CH$_2$—CH=CH—(CH$_2$)$_4$—CH$_3$, —(CH$_2$)$_7$—CH=CH—CH$_2$—CH(Y)—CH(Y)—(CH$_2$)$_4$—CH$_3$, —(CH$_2$)$_7$—CH(Y)—CH(Y)—CH$_2$—CH=CH—(CH$_2$)$_4$—CH$_3$, —(CH$_2$)$_7$—CH(Y)—CH(Y)—CH$_2$—CH(Y)—(CH$_2$)$_5$—CH$_3$, —(CH$_2$)$_8$—CH(Y)—CH$_2$—CH(Y)—CH(Y)—(CH$_2$)$_4$—CH$_3$, —(CH$_2$)$_7$—CH(Y)—CH$_2$—CH$_2$—CH(Y)—CH(Y)—(CH$_2$)$_4$—CH$_3$, —(CH$_2$)$_7$—CH(Y)—CH(Y)—CH$_2$—CH$_2$—CH(Y)—(CH$_2$)$_4$—CH$_3$, —(CH$_2$)$_7$—CH(Y)—CH(Y)—CH$_2$—CH(Y)—CH(Y)—(CH$_2$)$_4$—CH$_3$, —(CH$_2$)$_{14}$—CH$_3$, —(CH$_2$)$_{13}$—CH$_3$, where group Y, as described above, is selected from

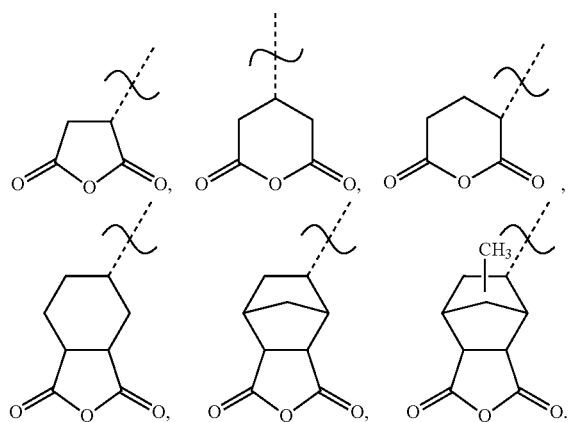

The connecting dotted lines on these groups stand for linkage sites linking the carbon atoms on R$^1$.

According to the present invention, the embodiments of group R$^2$ for example may include: carboxyl, methyl, ethyl, propyl, cyclopentyl, cyclohexyl, —CH$_2$—COOH (referring to be C1 alkyl substituted by a carboxyl group), —(CH$_2$)$_2$—COOH (referring to be C2 alkyl substituted by a carboxyl group), —CH(CH$_2$—COOH)$_2$ (referring to be C3 alkyl substituted by two carboxyl groups),

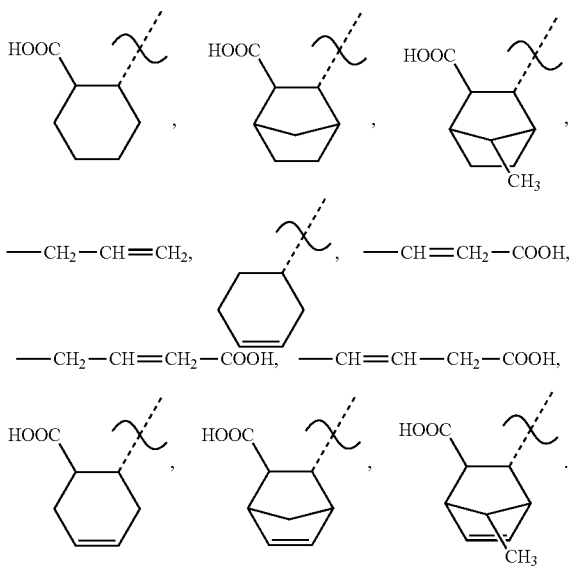

According to the present invention, the foregoing emulsifier may be a product available in the market and may also be prepared by a conventional method of the art. Preferably, the method for preparing the emulsifier comprises: subjecting a polyamine compound represented by Formula (2) to take amidation reaction with one or more of carboxylic acids represented by Formula R$^1$—COOH, and contacting and reacting the reaction product with one or more of carboxylic acids R$^2$—COOH and anhydrides thereof;

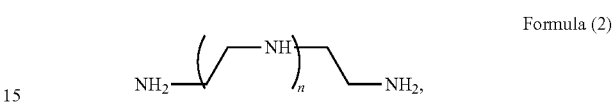

Formula (2)

where R$^2$ and n have been described above, so no necessary details will be given herein. R$^1$ is selected from C14-C30 alkyl and C14-C30 unsaturated alkyl with a carbon-carbon double bond.

The embodiments of the carboxylic acids represented by Formula R$^{1'}$—COOH for example may include: COOH—(CH$_2$)$_7$—CH=CH—(CH$_2$)$_7$—CH$_3$ (also called as oleic acid), COOH—(CH$_2$)$_7$—CH=CH—CH$_2$—CH=CH—(CH$_2$)$_4$—CH$_3$ (also called as linoleic acid), COOH—(CH$_2$)$_{16}$—CH$_3$ (also called as octadecanoic acid), COOH—(CH$_2$)$_{14}$—CH$_3$ (also called as hexadecanoic acid or palmitic acid), COOH—(CH$_2$)$_{13}$—CH$_3$ (also called as pentadecanoic acid).

The embodiments of carboxylic acids represented by Formula R$^2$—COOH and anhydrides thereof for example may include: HOOC—COOH (oxalate), CH$_3$—COOH (acetic acid), CH$_3$—COO—CO—CH$_3$ (acetic anhydride), HOOC—CH$_2$—COOH (malonic acid), HOOC—CH$_2$—CH$_2$—COOH (succinic acid), HOOC—CH$_2$—CH(COOH)—CH$_2$—COOH (tricarballylic acid),

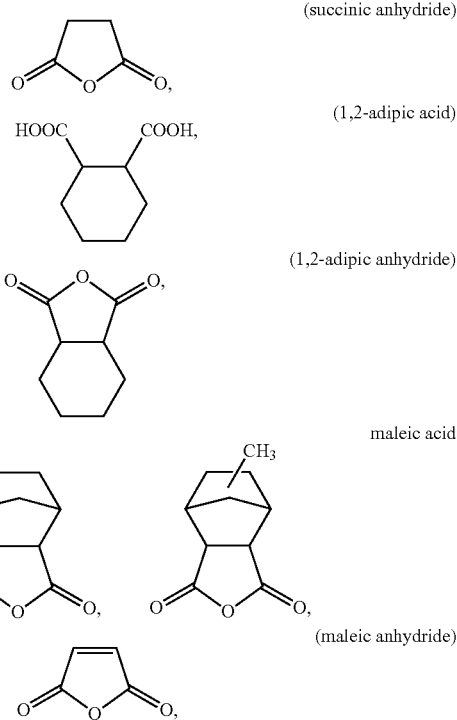

-continued

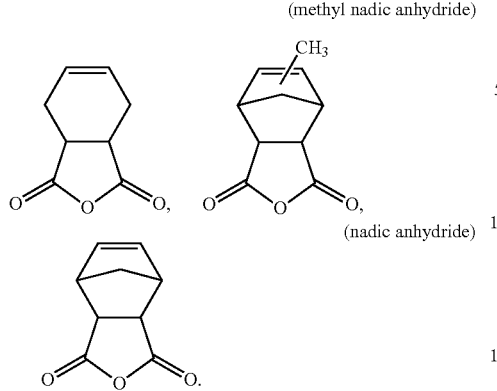
(methyl nadic anhydride)
(nadic anhydride)

According to the present invention, the embodiments of the polyamine represented by Formula (2) for example may include:

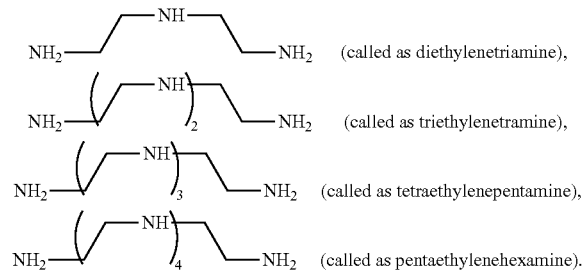
(called as diethylenetriamine),
(called as triethylenetramine),
(called as tetraethylenepentamine),
(called as pentaethylenehexamine).

According to the present invention, the amidation reaction between polyamine represented by foregoing Formula (2) and carboxylic acid represented by $R^{1'}$—COOH mainly refers to the amidation reaction between the primary amine of the polyamine represented by foregoing Formula (2) and the carboxylic group of the carboxylic acid represented by $R^{1'}$—COOH, with water molecules removed to form amido bonds, thereby obtaining one or more of compounds with secondary amine not substituted in the middle of the chain as represented by Formula

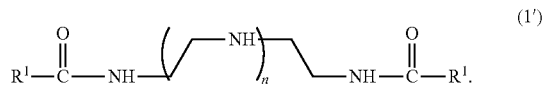 (1')

Preferably, the molar ratio of the polyamine compound represented by Formula (2) and the carboxylic acid represented by Formula $R^{1'}$—COOH is 1:1.8 to 1:3, preferably 1:1.8 to 1:2.2.

According to the present invention, preferably, the conditions of the amidation reaction comprise: the temperature is a temperature of 220-230° C., pH value of 7-9 and a time of 3-5 h. In order to make amidation reaction more sufficient, this method may further comprise: firstly mixing the polyamine represented by Formula (2) with one or more of carboxylic acids represented by $R^{1'}$—COOH for 10-30 min under a stirring rate of 80-300 r/min, then taking the amidation reaction under a stirring rate of 80-300 r/min, and water is trapped by water knockout trap during amidation reaction.

According to the present invention, the emulsifier of the present invention may be obtained through contacting and reacting the above reaction product of the amidation reaction with one or more of the carboxylic acids represented by $R^2$—COOH and anhydrides thereof. The reaction product of amidation reaction may be purified to obtain the compound represented by

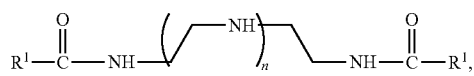

alternatively, the reaction product of amidation reaction without purification may directly contact and react with one or more of the carboxylic acids represented by $R^2$—COOH and anhydrides thereof so as to link —C(O)—$R^2$ substituent to the secondary amine between two amido bonds, thereby forming the compound with a comb-like structure represented by Formula (1). Preferably, the molar ratio of the polyamine compound represented by Formula (2) and the carboxylic acids represented by Formula $R^2$—COOH and anhydrides thereof is 1:0.5 to 1:20. For example, the molar ratio of the polyamine compound represented by Formula (2) and the carboxylic acids represented by Formula $R^2$—COOH and anhydrides thereof is 1:1.8 to 1:2.2, 1:3.6 to 1:4.4, 1:5.4 to 1:6.6, 1:7.2 to 1:8.8, 1:9 to 1:11, 1:10.8 to 1:13.2.

According to the present invention, when the carboxylic acid represented by $R^{1'}$—COOH is an unsaturated carboxylic acid with a carbon-carbon double bond, and the carboxylic acids represented by Formula $R^2$—COOH and anhydrides thereof adopted in the process of the contract reaction also contain a carbon-carbon double bond, then in the process of the contact reaction, addition reaction may also occur between the carbon-carbon double bond in the carboxylic acids represented by Formula $R^2$—COOH (and anhydrides thereof) and the carbon-carbon double bond in the reaction product of the amidation reaction, thereby obtaining the compound with $R^1$ (shown in Formula (1)) substituted by group Y. Although the present invention does not have particular limitation to this, the compound obtained under this case is also included in the emulsifier described in the present invention.

According to the present invention, preferably, the conditions of the contact reaction comprise: a temperature of 75-90° C., pH value of 7-9 and a time of 6-10 h. In order to make contact reaction more sufficient, this method may further comprise: contacting and reacting the reaction product of the amidation reaction with one or more of the carboxylic acids represented by Formula $R^2$—COOH and anhydrides thereof under a stirring rater of 200-500 r/min, and water is trapped by water knockout trap during the contact reaction.

According to the present invention, it should be noted that the emulsifier of the present invention may be one of the compounds represented by Formula (1), but if the foregoing preparation method is adopted, the emulsifier may also be one of the compounds represented by Formula (1) obtained through purifying and separating the product obtained by the foregoing preparation method. However, as more effective operation, the emulsifier of the present invention may be a plurality of the compounds represented by Formula (1), i.e.: if the foregoing preparation method is adopted, the emulsifier may be a product directly obtained by the foregoing preparation method and is used without purification. In other words, it may be understood that the emulsifier of the present invention is a product obtained by the foregoing method without purification.

According to the present invention, another important component of the composition of the present invention is the rheological modifier. As described above, the rheological modifier is a dimer acid-organic amine copolymer, of which the dimer acid is a dimer fatty acid containing two carboxylic groups, which is a dimer of oleic acid ($CH_3(CH_2)_7CH=CH(CH_2)_7COOH$)) and linoleic acid ($CH_3(CH_2)_4CH=CHCH_2CH=CH(CH_2)_7COOH$). Such dimer acid may be obtained by a conventional method of the present invention, for example the method recorded in literature "Zhang Shulin. Synthesis and application of dimer acid, Speciality Petrochemicals, 1995", or may be a product available in the market (preferably, the purity is 98 wt. % or above).

According to the present invention, in order to obtain a composition with performance more suitable for raising density and temperature resistance of oil-in-water drilling fluid, the alkylamine is preferably one or more of C12 alkyl primary amine, C13 alkyl primary amine, C14 alkyl primary amine, C15 alkyl primary amine, C16 alkyl primary amine, C17 alkyl primary amine and C18 alkyl primary amine, more preferably C12 alkyl primary amine and for C18 alkyl primary amine.

According to the present invention, in order to obtain a composition with performance more suitable for raising density and temperature resistance of oil-in-water drilling fluid, the arylamine is preferably one or more of aniline, 2-methylaniline, 3-methylaniline, 4-methylaniline, 2-ethylaniline, 3-ethylaniline, 4-ethylaniline, 2-propylaniline, 3-propylaniline and 4-propylaniline, more preferably one or more of aniline, 2-methylaniline, 3-methylaniline and 4-methylaniline.

In a preferred embodiment of the present invention, the dimer acid is a dimer of oleic acid and linoleic acid, the alkylamine is C12 alkyl primary amine or C18 alkyl primary amine, and the arylamine is aniline or 3-methylaniline.

According to the present invention, in order to obtain a composition with performance more suitable for raising density and temperature resistance of oil-in-water drilling fluid, the molar ratio of the structural units from the dimer acid, structural units from the alkylamine and structural units from the arylamine is preferably 1:0.3-1:0.2-1, more preferably 1:0.3-0.8:0.2-0.7, further more preferably 1:0.4-0.7:0.3-0.6.

Preferably, the weight-average molecular weight of the dimer acid-organic amine copolymer is 2,200-9,000 g/mol, and the absolute viscosity thereof is 20,000-150,000 cp. Considering from the perspective of obtaining a composition more suitable for raising density and temperature resistance of oil-in-water drilling fluid, more preferably the weight-average molecular weight of the dimer acid-organic amine copolymer is 4,000-9,000 g/mol, and the absolute viscosity thereof is 100,000-150,000 cp. More preferably, the weight-average molecular weight of the dimer acid-organic amine copolymer is 5,000-9,000 g/mol, and the absolute viscosity thereof is 100,000-150,000 cp. In the present invention, weight-average molecular weight is measured by GPC (gel permeation chromatography), and absolute viscosity is measured by Brookfield viscometer.

According to the present invention, the dimer acid-organic amine copolymer as rheological modifier may be prepared by a conventional method of the art. For example, the method for preparing the dimer acid-organic amine copolymer includes: copolymerizing the dimer acid, the alkylamine and the arylamine. In this method, the dimer acid, alkylamine and arylamine have been described above, so no necessary details will be given herein.

According to the present invention, the foregoing copolymerization reaction among dimer acid, alkylamine and arylamine is mostly dehydration condensation reaction between carboxylic acids and amines. By copolymerization reaction among dimer acid, alkylamine and arylamine in the present invention alone, a dimer acid-organic amine copolymer with good performance may be obtained as a rheological modifier of oil-in-water drilling fluid, but in order to obtain a rheological modifier with absolute viscosity and molecular weight more suitable for oil-in-water drilling fluid, the molar ratio of the dimer acid, alkylamine and arylamine is 1:0.3-1:0.2-1, more preferably 1:0.3-0.8:0.2-0.7, further more preferably 1:0.4-0.7:0.3-0.6.

According to the present invention, The copolymerization reaction may adopt a conventional method of the art as long as a dimer acid-organic amine copolymer that may be used as a rheological modifier of the composition can be obtained. Preferably, before copolymerization of dimer acid, alkylamine and arylamine, they are mixed to obtain a monomer mixture; then with the existence of concentrated sulfuric acid, the obtained monomer mixture takes copolymerization reaction.

According to the present invention, if the dimer acid, alkylamine and arylamine are mixed at first to obtain monomer mixture, the monomers can more sufficiently contact each other in the subsequent polymerization reaction. As the foregoing monomer mixture is sticky, preferably the mixing is conducted at higher temperature, and particularly preferably the adopted mixing conditions include: a temperature of 100-130° C. and a time of 20-30 min.

According to the present invention, when the foregoing concentrated sulfuric acid is used as a catalyst of the copolymerization reaction in the present invention, there is no particular limitation to its dose as long as it can catalyze the copolymerization reaction in the present invention. Preferably, based on the total weight of the dimer acid, alkylamine and arylamine, the dose of the concentrated sulfuric acid is 0.3-1 wt. %. The concentrated sulfuric acid may be a sulfuric acid solution with sulfuric acid concentration of 95 wt. % or above (preferably 98 wt. %).

According to the present invention, preferably, the conditions of the copolymerization reaction comprise: a temperature of 150-180° C. and a time of 2-6 h. More preferably, the conditions of the copolymerization reaction comprise: a temperature of 155-175° C. and a time of 2-6 h. Further more preferably, the conditions of the copolymerization reaction comprise: a temperature of 160-170° C. and a time of 2-6 h.

In order to promote the copolymerization reaction, byproduct water of copolymerization reaction may be removed from the reaction system. The method for removing byproduct water is a conventional method of the art, so no necessary details will be given here.

When the foregoing method is adopted to prepare dimer acid-organic amine copolymer, the rheological modifier may be either the dimer acid-organic amine copolymer prepared by the foregoing method, or a 50-70 wt. % solution obtained by directly using a diluent to dilute the dimer acid-organic amine copolymer prepared by the foregoing method (in other words, based on the total weight of the dimer acid-organic amine copolymer solution after dilution, the content of dimer acid-organic amine copolymer is 50-70 wt. %), or a rheological modifier of the present invention obtained by other methods well known in the art and containing the dimer acid-organic amine copolymer.

Those skilled in the art should understand that the product of copolymerization reaction is not separated in general and it is believed that all the adopted monomers basically take complete reaction and the product of copolymerization reaction is directly used as copolymer. Therefore, for the sake of convenience, the diluent may be directly added to the products of the copolymerization reaction after the copolymerization reaction in the method for preparing the foregoing dimer acid-organic amine copolymer is completed, and there is no need to purify and separate the dimer acid-organic amine copolymer in it. In a general sense, the dimer acid-organic amine copolymer referred to in the present invention is also the product of the copolymerization reaction without purification and separation, or the product of copolymerization reaction obtained after only byproduct water is removed as described above.

The diluent for example may be a diluent conventionally adopted in the art, such as tall oil and/or tall oil fatty acid.

According to the present invention, the additive composition may further comprise conventional additives of the art used in drilling fluid, for example may comprise one or more of filtrate reducer, formation sealant, heavy weight additive, CaO and humectant. When these other additives are added to drilling fluid, it may be understood that a drilling fluid is formed in a form of additive composition of the present invention. Of course, it may also be understood that these other additives are independently used as components of drilling fluid rather than the components of the composition of the present invention. All these are included in the scope of the present invention.

The present invention further provides a super high temperature super high density clay-free oil-in-water drilling fluid containing the foregoing additive composition.

According to the present invention, the super high temperature super high density clay-free oil-in-water drilling fluid contains the additive composition of the present invention, may achieve high temperature resistance and high density, and is particularly suitable for operation of high pressure deep wells. Preferably, based on the total weight of the drilling fluid, the content of the additive composition is 2 wt. % or lower, more preferably 1 wt. % or lower. Under the precondition of meeting the above conditions, preferably, the dose of the rheological modifier makes the content of the dimer acid-organic amine copolymer 1 wt. % or lower (preferably 0.5 wt. % or lower, more preferably 0.1 wt. % or lower, more preferably 0.01 wt. % or lower), and the dose of the emulsifier is 1 wt. % or lower (preferably 0.5 wt. % or lower, more preferably 0.1 wt. % or lower, more preferably below 0.02 wt. % or lower).

According to the present invention, the oil-in-water drilling fluid may further contain conventional additives used in clay-free oil-in-water drilling fluid, preferably, the oil-in-water drilling fluid contains one or more of filtrate reducer, formation sealant, heavy weight additive, CaO and humectant.

Among them, the filtrate reducer can improve well building property of drilling fluid during filtration, and for example may be one or more of sulfonated methyl phenol formaldehyde resin (for example SMP-I or SMP-II), sulfonated methyl lignite resin (for example SPNH) and zwitterionic polymer JT-888, preferably SMP-II and for SPNH. More preferably, the content of the filtrate reducer is 0.1-2 wt. %, more preferably 0.1-1 wt. %.

Among them, the humectant can improve the wettability of drilling fluid and prevent pipe-sticking and other complex down-hole conditions, for example may be one or more of modified phospholipid (modified phospholipid FHGT-G purchased from Shanghai Youchuang Industry Co., Ltd.) and fatty glyceride and surfactant mixture (for example FK-1), preferably modified phospholipid FHGT-G. More preferably, the content of the lubricant is 0.1-1 wt. %.

Among them, the formation sealant plays a role in improving the quality of filter cakes, and for example may be oil soluble polymer resin (grade S-160 polymer resin purchased from Shandong Deshunyuan Petroleum Technology Co., Ltd.). Preferably, the content of the formation sealant is 0.1-1 wt. %.

Among them, the heavy weight additive plays a role in regulating the density of drilling fluid to the needed density, and for example may be barite (for example, barite with barium sulfate content of above 90 wt. %). Preferably, the content of the heavy weight additive is 50-85 wt. %.

Among them, CaO plays a role in saponifying emulsifier and neutralizing down-hole acidic gas, and may be provided by calcium carbonate, calcium oxide, etc.

The foregoing additives may be products available in the market or prepared by conventional methods of the art, so no unnecessary details will be given here.

According to the present invention, the oil phase used as the super high temperature super high density clay-free oil-in-water drilling fluid may be provided by a conventional oil phase of the art used as drilling fluid. For example, it may be one or more of 3# white oil (the flash point is 220° C., the kinematic viscosity at 40° C. is 3 mm$^2$/s, and the specific gravity is 0.85), 5# white oil (the flash point is 220° C., the kinematic viscosity at 40° C. is 3.5 mm$^2$/s, and the specific gravity is 0.85), 7# white oil (the flash point is 220° C., the kinematic viscosity at 40° C. is 4.1 mm$^2$/s, and the specific gravity is 0.85), 10# white oil (the flash point is 220° C., the kinematic viscosity at 40° C. is 4.5 mm$^2$/s, and the specific gravity is 0.85) and 15# white oil (the flash point is 220° C., the kinematic viscosity at 40° C. is 5.6 mm$^2$/s, and the specific gravity is 0.85). The dose of the oil phase makes the oil-water ratio (volume ratio) of the drilling fluid be 85:15 to 94:6, preferably 90:10.

The water adopted may be conventional water of the art, preferably a $CaCl_2$ aqueous solution with $CaCl_2$ concentration of 20-40 wt. %.

According to the present invention, the super high temperature super high density clay-free oil-in-water drilling fluid can achieve high temperature resistance and high density. For example, the drilling fluid has a temperature resistance property resisting of 240° C. or above and its density is 2.6 g/cm$^3$ or above (before and after hot rolling, density can remain unchanged by and large).

EXAMPLES

In the examples below, weight-average molecular weight is measured by GPC (the experimental instrument is gel permeation chromatography of American Waters, and the model is E2695); molecular weight distribution coefficient is the ratio of weight-average molecular weight to number-average molecular weight measured by GPC.

Emulsifier Preparation Example 1

(1) The reactants at a molar ratio of tetraethylenepentamine: linoleic acid=1:2.2 (i.e. the molar ratio of the dose of the primary amine group on the tetraethylenepentamine and the dose of linoleic acid is 1:1.1) was mixed and stirred at 250 r/min for 40 min, subsequently the pH value of the obtained mixture was adjusted to 9, and then reacted at 230° C. for 3 h with a water knockout trap for water traping, and then the product was cooled to room temperature;

(2) The reaction product in step (1) was mixed with malonic acid (the molar ratio of the dose of tetraethylene-pentamine and the dose of malonic acid is 1:0.6), subsequently the pH value of the obtained mixture was adjusted to 8 and then reacted at 90° C. for 6 h under a stirring rate of 400 r/min to obtain emulsifier A1. Through analysis and determination of infrared spectroscopy, $^1$H-NMR and $^{13}$C-NMR, it was shown the emulsifier A1 contains amide group, unsaturated double bond and carboxyl and has a comb-like structure.

Emulsifier Preparation Example 2

(1) The reactants at a molar ratio of diethylenetriamine:oleic acid=1:2 (i.e. the molar ratio of the dose of the primary amine group on the and the dose of oleic acid is 1:1) was mixed and stirred at 250 r/min for 20 min, subsequently the pH value of the obtained mixture was adjusted to 7, and then reacted at 225° C. for 5 h with a water knockout trap for water traping, and then the product was cooled to room temperature;

(2) The reaction product in step (1) was mixed with oxalic acid (the molar ratio of the dose of diethylenetriamine and the dose of oxalic acid is 1:1.2), subsequently the pH value of the obtained mixture was adjusted to 7 and then reacted at 75° C. for 10 h under a stirring rate of 500 r/min to obtain emulsifier A2. Through analysis and determination of infrared spectroscopy, $^1$H-NMR and $^{13}$C-NMR, it was shown the emulsifier A2 contains amide group, unsaturated double bond and carboxyl and has a comb-like structure.

Emulsifier Preparation Example 3

(1) This step was operated by the same process in the step (1) of emulsifier preparation example 1;

(2) The reaction product in step (1) was mixed with maleic anhydride (the molar ratio between the dose of diethylenetriamine and the dose of maleic anhydride as to anhydride group is 1:1.2), subsequently the pH value of the obtained mixture was adjusted to 9 and then reacted at 80° C. for 8 h under a stirring rate of 500 r/min to obtain emulsifier A3. Through analysis and determination of infrared spectroscopy, $^1$H-NMR and $^{13}$C-NMR, it was shown the emulsifier A3 contains amide group, unsaturated double bond and carboxyl and has a comb-like structure and the long alkyl chain substituted with group

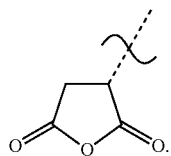

Rheological Modifier Preparation Example 1

(1) Dimer acid (purchased from Shanghai Hersbit Chemical Co., Ltd. with trade mark Pripol 1013, the same below), C12 alkyl primary amine and aniline at a molar ratio of 1:0.5:0.5 was added to a reaction vessel and stirred at 120±2° C. for 30 min to obtain a homogeneously mixed monomer mixture;

(2) A concentrated sulfuric acid (the concentration is 98 wt. %, and the dose is 0.5 wt. % of monomer mixture) was added dropwise to the foregoing monomer mixture (complete the addition in about 2 min) and the obtained mixture was reacted at 160±5° C. for 2 h in presence of condensing and discharging water devices. The obtained reaction product is dimer acid-organic amine copolymer. Its weight-average molecular weight is 6,500 g/mol and its absolute viscosity is 125,000 cp.

A diluent tall oil (purchased from Jinan Jinquan Chemical Co., Ltd., with trade mark F1, the same below) was added to dimer acid-organic amine copolymer to dilute dimer acid-organic amine copolymer to 50 wt. % and a rheological modifier B1 of the present invention was obtained. This liquid is an orange liquid.

Rheological Modifier Preparation Example 2

(1) Dimer acid, C12 alkyl primary amine and 3-methylaniline at a molar ratio of 1:0.5:0.5 was added to a reaction vessel and stirred at 120±2° C. for 30 min to obtain a homogeneously mixed monomer mixture;

(2) A concentrated sulfuric acid (the concentration is 98 wt. %, and the dose is 0.5 wt. % of monomer mixture) was added dropwise to the foregoing monomer mixture (complete the addition in about 2 min) and the obtained mixture was reacted at 170±5° C. for 6 h. The obtained reaction product is dimer acid-organic amine copolymer. Its weight-average molecular weight is 6,000 g/mol and its absolute viscosity is 118,000 cp.

A diluent tall oil was added to dimer acid-organic amine copolymer to dilute dimer acid-organic amine copolymer to 70 wt. % and a rheological modifier B2 of the present invention was obtained. This liquid is an orange liquid.

Rheological Modifier Comparative Example 1

According to the method in rheological modifier preparation example 1, but the difference is: n-pentylamine is adopted to replace C12 alkyl primary amine as one of monomers. The obtained reaction product is dimer acid-organic amine copolymer, its weight-average molecular weight is 3,800 g/mol and its absolute viscosity is 55,000 cp. Thus rheological modifier D1 is obtained. This liquid is an orange liquid.

Rheological Modifier Comparative Example 2

According to the method in rheological modifier preparation example 1, but the difference is: the adopted monomers are dimer acid and C12 alkyl primary amine at a molar ratio of 1:1, rather than aniline, the weight-average molecular weight of the obtained reaction product is 3,900 g/mol and the absolute viscosity is 57,000 cp. Thus rheological modifier D2 is obtained. This liquid is an orange liquid.

Embodiment 1

This embodiment is intended to illustrate the drilling fluid additive composition and super high temperature super high density clay-free oil-in-water drilling fluid of the present invention.

Formulation: 1 wt. % of CaO, 0.01 wt. % of the emulsifier A1, 0.005 wt. % of the rheological modifier B2 (calculated by dimer acid-organic amine copolymer), 80 wt. % of barite (purchased from Sichuan Zhengrong Industrial Co., Ltd.), and with a rest amount of $CaCl_2$ aqueous solution (in this solution, CaCl$_2$ concentration is 30 wt. %) and 3# white oil (purchased from Hangzhou Fuda Fine Oil Products Co., Ltd.)(oil-water ratio is 90:10); drilling fluid X1 is obtained. The density is 2.61 g/cm$^3$.

Embodiment 2

This embodiment is intended to illustrate the drilling fluid additive composition and super high temperature super high density clay-free oil-in-water drilling fluid of the present invention.

According to the formulation in Embodiment 1, but the difference is: the emulsifier A3 is adopted to replace emulsifier A1 and the dose of the rheological modifier B2 is 0.01 wt. %. Thus drilling fluid X2 is obtained. The density is 2.61 g/cm$^3$.

Embodiment 3

This embodiment is intended to illustrate the drilling fluid additive composition and super high temperature super high density clay-free oil-in-water drilling fluid of the present invention. According to the formulation in Embodiment 1, but the difference is: the dose of the emulsifier A1 is 0.02 wt. %. Thus drilling fluid X3 is obtained. The density is 2.61 g/cm$^3$.

Embodiment 4

This embodiment is intended to illustrate the drilling fluid additive composition and super high temperature super high density clay-free oil-in-water drilling fluid of the present invention. According to the formulation in Embodiment 2, but the difference is: the dose of the emulsifier A3 is 0.02 wt. %. Thus drilling fluid X4 is obtained. The density is 2.61 g/cm$^3$.

Comparative Example 1

According to the formulation in Embodiment 1, but the difference is: calcium naphthenate emulsifier (purchased from Hubei Shengtian Hengchuang Biotechnology Co., Ltd. With trade mark ZHC-2ZHC-3ZHC-4) is adopted to replace emulsifier A1. Thus drilling fluid DX1 is obtained. The density is 2.61 g/cm$^3$.

Comparative Example 2

According to the formulation in Embodiment 1, but the difference is: the rheological modifier D1 is adopted to replace B2. Thus drilling fluid DX2 is obtained. The density is 2.61 g/cm$^3$.

Comparative Example 3

According to the formulation in Embodiment 1, but the difference is: the rheological modifier D2 is adopted to replace B2. Thus drilling fluid DX3 is obtained. The density is 2.61 g/cm$^3$.

Test Example 1

After drilling fluid X1-X4 and DX1-DX3 were hot rolled at 220° C. for 16 h and at 240° C. for 16 h respectively, plastic viscosity (PV), apparent viscosity (AV), yield point (YP), initial gel strength (IGS), final gel strength (FGS), emulsion breaking voltage (or electric stability) (ES) and HTHP at room temperature were measured. The results are shown in Table 1. To be specific:

PV was measured by a Fann 6-speed viscometer by the method specified in China national standard GB/T29170-2012. The unit is mPa·s.

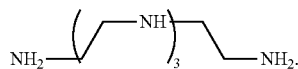

AV was measured by a Fann 6-speed viscometer by the method specified in China national standard GB/T29170-2012. The unit is mPa·s.

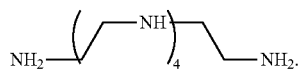

YP was measured by a Fann 6-speed viscometer by the method specified in China national standard GB/T29170-2012.

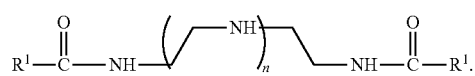

The unit is Pa.

IGS and FGS were measured by a Fann 6-speed viscometer by the method specified in China national standard GB/T29170-2012. The unit is Pa:

IGS=0.511θ$_3$(10 s)

FGS=0.511θ$_3$(10 min).

ES was measured by an electric stabilizer by the method specified in China petrochemical industry standard SH/T0549-1994. The unit is V.

HTHP refers to high temperature high pressure filter loss. It was measured by high temperature high pressure filter tester according to the method specified in China national standard GB/T29170-2012. The unit is mL.

TABLE 1

| Drilling fluid | PV mPa·s | AV mPa·s | YP Pa | IGS Pa | FGS Pa | ES V | HTHP mL | Density g/cm$^3$ |
|---|---|---|---|---|---|---|---|---|
| After hot rolling at 220° C. for 16 h | | | | | | | | |
| X1 | 110 | 114 | 4 | 4 | 5 | 841 | 16 | 2.61 |
| X2 | 121 | 138 | 17 | 6 | 8 | 874 | 16 | 2.61 |
| X3 | 109 | 112 | 3 | 5 | 6 | 998 | 12 | 2.61 |
| X4 | 123 | 144 | 21 | 8 | 12 | 1075 | 10 | 2.61 |
| DX1 | 115 | 120 | 5 | 2 | 3 | 684 | 18 | 2.61 |
| DX2 | 110 | 114 | 4 | 1 | 2 | 642 | 22 | 2.59 |
| DX3 | 102 | 104 | 2 | 2 | 3 | 623 | 19 | 2.6 |
| After hot rolling at 240° C. for 16 h | | | | | | | | |
| X1 | 121 | 123 | 2 | 1 | 2 | 778 | 18 | 2.61 |
| X2 | 144 | 148 | 4 | 3 | 5 | 887 | 16 | 2.61 |
| X3 | 119 | 122 | 3 | 1 | 2 | 797 | 16 | 2.61 |
| X4 | 143 | 147 | 4 | 3 | 5 | 975 | 12 | 2.61 |
| DX1 | 121 | 123 | 2 | 0.5 | 1 | 665 | 20 | 2.61 |
| DX2 | 115 | 118 | 3 | 0.5 | 1 | 525 | 24 | 2.61 |
| DX3 | 110 | 112 | 2 | 1 | 2 | 514 | 20 | 2.58 |

The data in Table 1 indicates that after the super high temperature super high density clay-free oil-in-water drilling fluid containing additive composition of the present invention was hot rolled at 240° C., HTHP was below 20 mL, ES was much larger than the ES of the drilling fluids in comparative examples, and the fluid still could have good rheological property, stability and temperature resistance.

Embodiment 5

This embodiment is intended to illustrate the drilling fluid additive composition and super high temperature super high density clay-free oil-in-water drilling fluid of the present invention.

Formulation: 1 wt. % of CaO, 0.01 wt. % of the emulsifier A2, 0.005 wt. % of the rheological modifier B1 (calculated by dimer acid-organic amine copolymer), 80 wt. % of barite (purchased from Sichuan Zhengrong Industrial Co., Ltd.), 0.4 wt. % of lubricant (modified phospholipid FHGT-G purchased from Shanghai Youchuang Industry Co., Ltd.), 0.2 wt. % of formation sealant (polymer resin filtrate reducer S-160 purchased from Shandong Deshunyuan Petroleum Technology Co., Ltd.), and with a rest amount of $CaCl_2$ aqueous solution (in this solution, $CaCl_2$ concentration is 30 wt. %) and 3# white oil (purchased from Hangzhou Fuda Fine Oil Products Co., Ltd.)(oil-water ratio is 90:10); drilling fluid X5 is obtained. The density is 2.61 $g/cm^3$.

Embodiment 6

This embodiment is intended to illustrate the drilling fluid additive composition and super high temperature super high density clay-free oil-in-water drilling fluid of the present invention.

According to the formulation in Embodiment 5, but the difference is: 0.01 wt. % of the rheological modifier B1, 0.3 wt. % of the humectant and 0.4 wt. % of the formation sealant are adopted to obtain drilling fluid X6, with a density of 2.61 $g/cm^3$.

Embodiment 7

This embodiment is intended to illustrate the drilling fluid additive composition and super high temperature super high density clay-free oil-in-water drilling fluid of the present invention.

According to the formulation in Embodiment 5, but the difference is: 0.02 wt. % of the emulsifier A2 is adopted to obtain drilling fluid X7, with a density of 2.61 $g/cm^3$.

Embodiment 8

This embodiment is intended to illustrate the drilling fluid additive composition and super high temperature super high density clay-free oil-in-water drilling fluid of the present invention.

According to the formulation in Embodiment 6, but the difference is: 0.02 wt. % of the emulsifier A2 is adopted to obtain drilling fluid X8, with a density of 2.61 $g/cm^3$.

Comparative Example 4

According to the formulation in Embodiment 8, but the difference is: the emulsifier EZ-MUL (emulsifier EZ MUL® NS purchased from Halliburton company) is adopted to replace the emulsifier A1, and rheological modifier HRP (rheological modifier HRP® NS purchased from Halliburton company) is adopted to replace the rheological modifier B1, thereby obtaining drilling fluid DX4, with a density of 2.61 $g/cm^3$.

Comparative Example 5

According to the formulation in Embodiment 8, but the difference is: the emulsifier VERSO-MUL (emulsifier CARBO-MUL-DRILL™ purchased from Baker Hughes) is adopted to replace the emulsifier A1, and rheological modifier CARBO-MOD (rheological modifier CARBO-MOD-DRILL™ purchased from Baker Hughes) is adopted to replace the rheological modifier B1, thereby obtaining drilling fluid DX5, with a density of 2.61 $g/cm^3$.

Test Example 2

The method in Test Example 1 was adopted. After drilling fluid X5-X8 and DX4-DX5 were separately hot rolled at 240° C. for 16 h, PV, AV, YP, IGS, FGS, ES and HTHP at room temperature were measured. The results are shown in Table 2.

TABLE 2

| Drilling fluid | PV mPa·s | AV mPa·s | YP Pa | IGS Pa | FGS Pa | ES V | HTHP mL | Density $g/cm^3$ |
|---|---|---|---|---|---|---|---|---|
| After hot rolling at 24° C. for 16 h | | | | | | | | |
| X5 | 125 | 127 | 2 | 3 | 6 | 1678 | 8.3 | 2.61 |
| X6 | 139 | 146 | 7 | 4 | 8 | 2000+ | 7.2 | 2.61 |
| X7 | 123 | 126 | 3 | 4 | 7 | 1697 | 8.2 | 2.61 |
| X8 | 138 | 141 | 5 | 3 | 5 | 2000+ | 7.6 | 2.61 |
| DX4 | 139 | 141 | 2 | 2 | 3 | 770 | 8.4 | 2.61 |
| DX5 | 147 | 149 | 2 | 1 | 2 | 525 | 8.8 | 2.61 |

The data in Table 2 indicates that after the super high temperature super high density clay-free oil-in-water drilling fluid containing additive composition of the present invention was hot rolled at 240° C., HTHP was below 10 mL, ES was much larger than the ES of the drilling fluids in comparative examples (prepared based on products of foreign companies), and the fluid could acquire higher rheological property and better temperature resistance after aging.

Above the preferred embodiments of the present invention are described in details, but the present invention is not limited to the concrete details of the foregoing embodiments. Within the scope of the technical conception of the present invention, the technical scheme of the present invention may have various simple modifications. They all shall be within the scope of protection of the present invention.

The described and illustrated embodiments are to be considered as illustrative and not restrictive in character, it being understood that only the specific embodiments according to the invention have been shown and described and that all changes and modifications that come within the scope of the invention, as set out in the accompanying claims are desired to be protected. It should be understood that while the use of words such as "preferable", "preferably", "preferred" or "more preferred" in the description suggest that a feature so described may be desirable, it may nevertheless not be necessary and embodiments lacking such a feature may be contemplated as within the scope of the invention as defined in the appended claims. In relation to the claims, it is intended that when words such as "a," "an," "at least one," or "one" are used to preface a feature there is no intention to limit the claim to only one such feature unless specifically stated to the contrary in the claim.

Besides, it should be noted that the concrete technical features described in the foregoing embodiments may be combined in any appropriate way under the condition of no conflict. In order to avoid unnecessary repetition, all the possible combinations of the present invention are not described separately.

Further, the embodiments of the present invention may be freely combined provided that such combinations won't go against the thinking of the present invention. Likewise, they should also be deemed as the content disclosed by the present invention.

The invention claimed is:

1. A drilling fluid additive comprising an emulsifier and a rheological modifier; the emulsifier is represented by Formula (1):

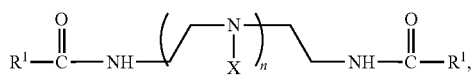

Formula (1)

the rheological modifier is a dimer acid-organic amine copolymer comprising structural units from a dimer acid, structural units from an alkylamine and structural units from an arylamine, wherein the dimer acid is a dimer of oleic acid and linoleic acid, the alkylamine is one or more of C10-C20 alkyl primary amines, and the arylamine is one or more of aniline and aniline substituted by C1-C3 alkyl at one or more sites on benzene ring, wherein each $R^1$ is independently selected from C14-C30 alkyl optionally substituted by Y and C14-C30 unsaturated alkyl optionally substituted by group Y, and Y is independently selected from the following:

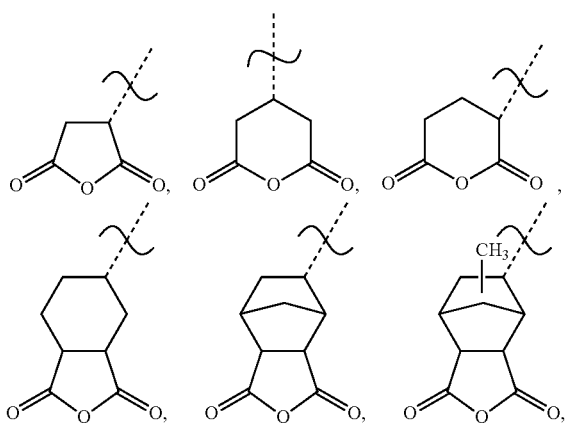

n is 1-8;
each X is independently selected from H and —C(O)—$R^2$, and at least one X is —C(O)—$R^2$, $R^2$ is selected from carboxyl, C1-C6 alkyl, C3-C8 cycloalkyl, C1-C6 alkyl substituted by carboxyl, C3-C8 cycloalkyl substituted by carboxyl, C3-C8 cycloalkyl substituted by carboxyl and C1-C4 alkyl, C2-C6 unsaturated alkyl, C3-C8 unsaturated cycloalkyl, C2-C6 unsaturated alkyl substituted by carboxyl, and C3-C8 unsaturated cycloalkyl substituted by carboxyl and C1-C4 alkyl.

2. The composition according to claim 1, wherein each $R^1$ is independently selected from C14-C20 alkyl optionally substituted by group Y and C14-C20 unsaturated alkyl optionally substituted by Y; n is 1-6; $R^2$ is selected from carboxyl, C1-C4 alkyl, C4-C6 cycloalkyl, C1-C4 alkyl substituted by carboxyl, C4-C6 cycloalkyl substituted by carboxyl, C4-C6 cycloalkyl substituted by carboxyl and methyl, C2-C4 unsaturated alkyl, C4-C6 unsaturated cycloalkyl, C2-C4 unsaturated alkyl substituted by carboxyl, and C4-C7 unsaturated cycloalkyl substituted by carboxyl and methyl.

3. The composition according to claim 2, wherein each $R^1$ is independently selected from C15-C18 alkyl optionally substituted by Y and C15-C18 unsaturated alkyl optionally substituted by Y; n is 1-4.

4. The composition according to claim 1, wherein the alkylamine is one or more of C12 alkyl primary amine, C13 alkyl primary amine, C14 alkyl primary amine, C15 alkyl primary amine, C16 alkyl primary amine, C17 alkyl primary amine and C18 alkyl primary amine; the arylamine is one or more of aniline, 2-methylaniline, 3-methylaniline, 4-methylaniline, 2-ethylaniline, 3-ethylaniline, 4-ethylaniline, 2-propylaniline, 3-propylaniline and 4-propylaniline.

5. The composition according to claim 4, wherein a molar ratio of the structural units from the dimer acid, structural units from the alkylamine and structural units from the arylamine is 1:0.3-1:0.2-1.

6. The composition according to claim 5, wherein a molar ratio of the structural units from the dimer acid, structural units from the alkylamine and structural units from the arylamine 1:0.3-0.8:0.2-0.7.

7. The composition according to claim 6, wherein a molar ratio of the structural units from the dimer acid, structural units from the alkylamine and structural units from the arylamine 1:0.4-0.7:0.3-0.6.

8. The composition according to claim 1, wherein the dimer acid-organic amine copolymer is prepared by copolymerizing the dimer acid, the alkylamine and the arylamine, wherein a molar ratio of the dimer acid, the alkylamine and the arylamine is 1:0.3-1:0.2-1.

9. The composition according to claim 8, wherein the conditions of the copolymerization reaction comprise: a temperature of 150-180° C. and a time of 2-6 h.

10. The composition according to claim 1, wherein a weight-average molecular weight of the dimer acid-organic amine copolymer is 2,200-9,000 g/mol, and the absolute viscosity of the copolymer is 20,000-150,000 cp.

11. The composition according to claim 10, wherein a weight-average molecular weight of the dimer acid-organic amine copolymer is 4,000-9,000 g/mol, and the absolute viscosity of the copolymer is 100,000-150,000 cp.

12. The composition according to claim 1, wherein a weight ratio of the emulsifier and the rheological modifier is 100:5 to 100:200.

13. The composition according to claim 12, wherein a weight ratio of the emulsifier and the rheological modifier is 100:5 to 100:100.

14. A method for the preparation of an emulsifier for use in a drilling fluid, the method comprising
(1) reacting a polyamine represented by Formula (2):

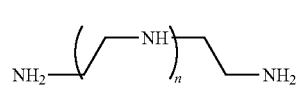

Formula (2)

with one or more carboxylic acids represented by $R^{1'}$—COOH to form an amide reaction product, and (2) reacting said reaction product with one or more carboxylic acids represented by $R^2$—COOH and anhydrides thereof; where, $R^{1'}$ is selected from C14-C30 alkyl and C14-C30 unsaturated alkyl.

15. The method according to claim 14, wherein the molar ratio between the polyamine compound represented by Formula (2) and the carboxylic acids represented by $R^{1'}$—COOH is 1:1.8 to 1:3; the molar ratio between the polyamine compound represented by Formula (2) and the carboxylic acids represented by $R^2$—COOH and anhydrides thereof is 1:0.5 to 1:20.

16. The method according to claim 14, wherein the conditions of (1) comprise: a temperature of 220-230° C., pH value of 7-9 and a time of 3-5 h.

17. The method according to claim 14, wherein the conditions of contact reaction comprise: a temperature of 75-90° C., pH value of 7-9 and a time of 6-10 h.

18. A super high temperature super high density clay-free oil-in-water drilling fluid, containing the additive composition according to claim 1.

19. The drilling fluid according to claim 18, wherein based on the total weight of the drilling fluid, the content of the additive composition is 2 wt. % or lower.

20. The drilling fluid according to claim 18, wherein the drilling fluid has a temperature resistance property resisting a temperature of 240° C. or above and its density is 2.6 g/cm$^3$ or above.

\* \* \* \* \*